| (12) | United States Patent | (10) Patent No.: | US 7,371,330 B2 |
|---|---|---|---|
| | Ducree et al. | (45) Date of Patent: | May 13, 2008 |

(54) PARTICLE SEDIMENTATION APPARATUS AND METHOD FOR PERFORMING PARTICLE SEDIMENTATION

(75) Inventors: Jens Ducree, Freiburg (DE); Roland Zengerle, Waldkirch (DE); Stefan Haeberle, Huerben (DE); Thilo Brenner, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 0 days.

(21) Appl. No.: 11/690,731

(22) Filed: Mar. 23, 2007

(65) Prior Publication Data

US 2007/0262034 A1    Nov. 15, 2007

Related U.S. Application Data

(63) Continuation of application No. PCT/EP2005/010341, filed on Sep. 23, 2005.

(30) Foreign Application Priority Data

Sep. 24, 2004    (DE) ................ 10 2004 046 396

(51) Int. Cl.
 *B01D 21/26*    (2006.01)
 *B04B 5/04*     (2006.01)
(52) U.S. Cl. ................ 210/787; 210/782; 422/64; 422/72; 422/101; 436/45; 436/177
(58) Field of Classification Search ............ 210/782, 210/787; 422/64, 72, 101; 436/45, 177

See application file for complete search history.

(56) References Cited

U.S. PATENT DOCUMENTS 4,010,894 A    3/1977 Kellogg (Continued)

FOREIGN PATENT DOCUMENTS

DE    3723092    1/1989

(Continued)

OTHER PUBLICATIONS

English Translation of the International Preliminary Report on Patentability for International Patent Application No. PCT/EP2005/010341.*

*Primary Examiner*—David A Reifsnyder
(74) *Attorney, Agent, or Firm*—Glenn Patent Group; Michael A. Glenn

(57) ABSTRACT

A particle sedimentation apparatus includes a rotation body rotatable about a rotation axis and a separation chamber formed in the rotation body, to cause sedimentation of particle suspension in the separation chamber upon rotation of the rotation body. The particles accumulate in a radially outward region of the separation chamber. A flow-rate-determining inflow channel having azimuthal path length with an inflow channel inlet and an inflow channel outlet is formed in the rotation body, the inflow channel inlet being arranged radially further inwardly than the inflow channel outlet, the inflow channel outlet being fluidically connected to the separation chamber and formed to introduce particle suspension into the separation chamber upon rotation of the rotation body. Furthermore, an outflow channel is formed in the rotation body with an outflow channel inlet and an outflow channel outlet, to at least partially drain supernatant liquid formed by sedimentation from the separation chamber.

3 Claims, 6 Drawing Sheets

U.S. PATENT DOCUMENTS

| | | |
|---|---|---|
| 4,469,793 A | 9/1984 | Guigan |
| 4,950,220 A | 8/1990 | Wells |
| 5,472,603 A | 12/1995 | Schembri |
| 6,548,788 B2 * | 4/2003 | Kellogg et al. ............. 219/543 |
| 6,818,435 B2 * | 11/2004 | Carvalho et al. ........ 435/286.5 |
| 2002/0027133 A1 | 3/2002 | Kellogg |

FOREIGN PATENT DOCUMENTS

| | | |
|---|---|---|
| EP | 0322657 | 7/1989 |
| EP | 0 608 006 A2 | 7/1994 |
| GB | 29640 | 0/1915 |
| WO | WO00/79285 | 12/2000 |
| WO | WO2004/061413 | 7/2004 |
| WO | WO 2006032529 A1 * | 3/2006 |

* cited by examiner

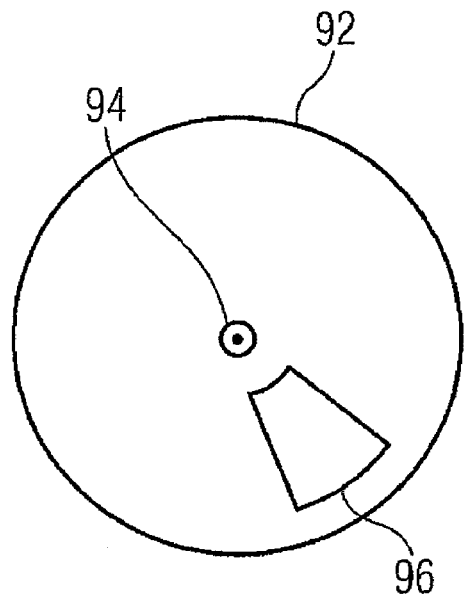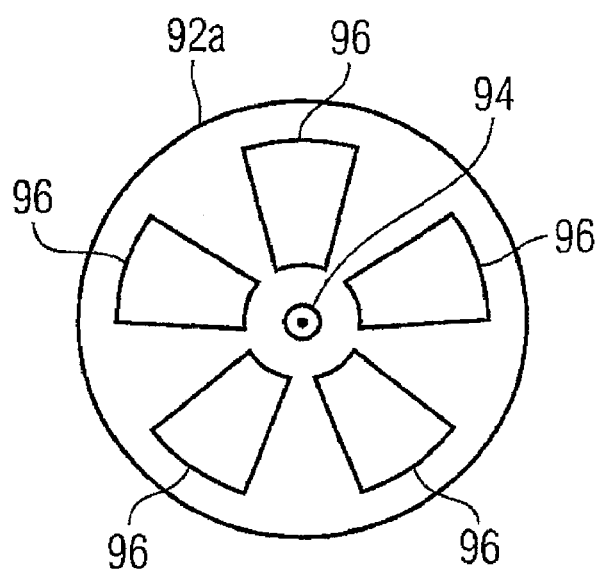
FIGURE 7A    FIGURE 7B
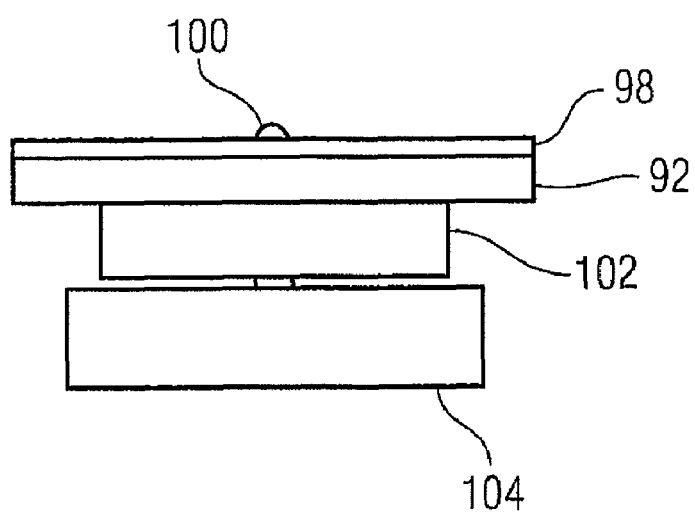
FIGURE 8

PARTICLE SEDIMENTATION APPARATUS AND METHOD FOR PERFORMING PARTICLE SEDIMENTATION

CROSS-REFERENCE TO RELATED APPLICATIONS

This application is a continuation of copending International Application No. PCT/EP2005/010341, filed Sep. 23, 2005, which designated the United States and was not published in English.

TECHNICAL FIELD

The present invention relates to a particle sedimentation apparatus and a method for performing particle sedimentation, utilizing centrifugal force.

BACKGROUND

The preparation of samples usually is the first step of many bioanalytical protocols on real samples, such as blood, food, or environmental samples. Often, a particular species of biomolecules is isolated from a mixture of other molecules and particle constituents and transferred into a new buffer. The invention described here concerns the centrifugal separation of particles from a suspension in which particles are suspended in a liquid.

Separating particles from suspensions by means of centrifuges represents an established standard method in laboratory analyses. Particles in suspension, such as the cellular proportion of blood, sediment under the influence of the centrifugal gravitational field according to their distribution of density. The particle suspension, for example the blood, is introduced into a rotating reservoir 10 (FIG. 1), which is rotatable about a rotation center 12. During rotation, for example at an angular velocity $\omega$, a stack of three phases forms in the reservoir 10, as shown in FIG. 1. A particle-free supernatant liquid forms radially inwardly, whereas at the radially outward edge a phase of sedimented particles 16 forms due to its mass density, which is increased as opposed to the liquid. In the sedimentation, this outer phase 16 mainly represents a sediment of more dense, cellular blood constituents, consisting of cells. Between the particle-free supernatant 14 and the sediment, there initially still is a phase 18 consisting of particles in suspension. After a certain time, the phase 18 transitions into the particle-free supernatant 14 with its liquid proportion and into the sediment 16 with its particle proportion.

The complete transition is reached after a time $t_1$, wherein at this time instant an equilibrium state is present in that particles and solution are separated from each other as far as possible, except for some liquid residue in the spaces between the sediment particles. As shown in FIG. 1, the interfaces between particle-free supernatant 14 and suspension 18, as well as between suspension 18 and sedimented particles 16 converge until the equilibrium is finally reached at the time instant $t_1$. In FIG. 1, the distribution in the reservoir is shown at a time instant $t_0$.

Following the sedimentation, the particle-free supernatant liquid is poured off the precipitate or taken out of the reservoir by means of a pipette.

Miniaturized analysis systems on rotating discs offer the simple possibility to sediment particles from suspensions, due to their centrifugal drive. But for further integrated process execution, in most cases the spatial separation of both phases from each other is required. The concluding procedure of pouring out or pipetting off, in particular, is difficult to represent technologically on this integrated microsystem, because the macroscopic method would correspond to a tilt of the channel axis with respect to the direction of the centrifugal force. Due to the further rotation axis, however, this could only be effected with significantly increased instrumental effort.

As it has been mentioned, an important goal with medical diagnostic systems is the integration of complete process chains from the preparation of blood to an analytical result. Various, so-called "lab on a chip" systems have been proposed, see M. J. Madou and G. J. Kellogg, Proc. Of SPIE, vol. 3259, 1998, pages 80-93; G. Thorsen, G. Ekstrand, U. Selditz, S. R. Wallenborg, and P. Andersson, Proc. Of UTAS 2003, eds. M. A. Northrup, K. F. Jenson, D. J. Harrison, Kluwer Academic, 2003, pages 457-460.

Various microfluidic structures on centrifugal platforms are known. These include, among others, sample preparation, flow control by capillary valves and further fluidic networks, see WO 0079285, WO 2004058406, WO 03024598. Furthermore, systems for the separation of blood into plasma and cells in non-centrifugally driven Microsystems are known, see WO 2004074846, WO 2004029221.

WO 2004/061413 A2 concerns a microfluidic apparatus enabling separation of particles in a liquid sample, and particularly of blood into its components, for further analysis. The separation into red blood cells and plasma takes place during few seconds after the blood sample has been introduced into a separation chamber by centrifugal force. A radially passing feed channel, leading into the separation chamber at a radial internal wall, is provided. The separation mechanism here critically depends on surface interactions.

From DE 3723092 C1, a passage centrifuge for industrial production of proteins from human blood plasma is known, in which plastic containers are arranged, which are arranged concentrically with respect to each other in a centrifugal drum, are mutually connected in the bottom region by at least one channel, form annular or ring-segment-shaped chambers, and of which the plastic container or containers facing the rotational axis of the centrifugal drum have an inflow port and the plastic container or containers provided in the outer region of the centrifugal drum have an overhead outflow channel.

In U.S. Pat. No. 4,010,894, a fluid container for use in a centrifugal system for separating the different constituents of blood is described. The container includes two circular layers of flexible material, having center openings. The outer peripheral edges and the inner annular portions around the center opening are connected to each other. Concentrically arranged inner and outer annular channels are formed at the outer peripheral portion of the assembly. Radial arcuate portions are connected to each other, whereby interrupted annular channels are formed. At a first end of the inner annular channel, an inlet tube is provided, which extends outwardly from the center opening and communicates with the first end of the inner annular channel. At the outlet or second end of the inner annular channel, a radially extending interchannel connector is provided, which comprises a sealed portion extending between the adjacent ends of the inner and outer annular channels. At this outlet end of the inner channel, also a radially enlarged region is provided, which acts as a first collecting chamber, into which an outlet tube extending from the inner opening leads. A second outlet chamber is provided at the outlet end of the outer annular channel.

SUMMARY

According to an embodiment, a method for performing sedimentation of a particle suspension, using micro-fluidic structures having an inflow channel having an azimuthal path length and determining the flow rate, wherein an in-flow channel inlet is arranged radially further inwardly than an inflow channel outlet, as well as a separation chamber with a particle accumulation region, and an outflow channel, which are formed in a rotation body, wherein a portion of the inflow channel with an azimuthal path length leads into the separation chamber, may have the steps of: imparting the rotation body with rotation at the given rotation frequency, in order to feed a defined particle suspension volume by centrifugal force through the inflow channel into the separation chamber at a position radially inward with respect to the particle accumulation region; sediment the particle suspension in the separation chamber, so that particles accumulate in a radially outward particle accumulation region of the separation chamber due to their higher mass density as compared with a liquid in the particle suspension; and at least partially draining off supernatant liquid developing by the sedimentation by centrifugal force through an outflow channel fluidically connected to the separation chamber, wherein the inflow channel has such a radial slope, such a length and such a cross section that, at a given rotation frequency and the defined particle suspension volume, the flow rate of the particle suspension into the separation chamber is so low that an inflow of a particulate phase in the separation chamber is forced along a wall spaced from an outflow channel inlet, so that an interface forming between supernatant liquid and a particulate phase in the separation chamber remains radially outside an outflow channel inlet, at which the outflow channel is fluidically connected to the separation chamber.

The present invention provides a particle sedimentation apparatus, comprising:

a rotation body rotatable about a rotation axis;

a separation chamber formed in the rotation body, which is formed to cause, upon rotation of the rotation body, sedimentation of a particle suspension in the separation chamber, in which particles accumulate in a radially outward region of the separation chamber;

an inflow channel, which is formed in the rotation body, has an azimuthal path length and determines the flow rate, with an inflow channel inlet and an inflow channel outlet, wherein the inflow channel inlet is arranged radially further inwardly than the inflow channel outlet, wherein the inflow channel outlet is fluidically connected to the separation chamber and formed to introduce a particle suspension into the separation chamber upon rotation of the rotation body; and an outflow channel formed in the rotation body with an outflow channel inlet and an outflow channel outlet, wherein the outflow channel inlet is arranged radially further inwardly than the outflow channel outlet, wherein the outflow channel inlet is fluidically connected to the separation chamber, wherein the outflow channel is formed to at least partially drain off supernatant liquid, which is formed by sedimentation caused by rotation of the rotation body, from the separation chamber.

The present invention further provides a method for performing sedimentation of a particle suspension, comprising the steps of:

feeding a particle suspension by centrifugal force through a flow-rate-determining inflow channel having an azimuthal path length into a separation chamber;

sedimenting the particle suspension in the separation chamber, so that particles accumulate in a radially outward region of the separation chamber due to their higher mass density as compared with a liquid in the suspension; and at least partially draining off supernatant liquid developing by the sedimentation by centrifugal force through an outflow channel fluidically connected to the separation chamber.

The present invention provides an apparatus and a method enabling continuous centrifugal extraction of particles from a solution for a finite time interval. Preferably, a defined volume of the supernatant is then centrifugally removed from the separation vessel, i.e. the separation chamber, and preferably metered at the same time.

In other words, the present invention in preferred embodiments provides a fluidic network rotating about a rotation center and being perpendicular to the rotation axis with components in the rotation plane, which comprises a separation chamber with defined volume capacity, an inflow channel and an outflow channel. The separation chamber is connected, for example, laterally above its bottom to a radially outward passing inflow channel, which determines the radially inward migration velocity of the overall fill height in the separation chamber through its rotation frequency and its radial slope, as well as its length and its cross section. The outflow channel is connected to the separation chamber above its bottom on the side opposite the inflow channel, for example, and radially decreases after a radial minimum thereof, wherein a defined volume part of the particle-free supernatant flows off from the same, for example into downstream structures. Preferably, the radial migration velocity of the overall fill height with reference to the radial position and the geometry of the outflow channel is choked strongly so that suspended particles do not get into the outlet channel at any time.

In preferred embodiments of the present invention, the inlet of the inflow channel is connected to a means for metering a liquid volume arranged radially further inward, so that the particle-free volume extracted through the outflow channel is fixedly defined by the dead volume of the channel structure (inflow channel, separation chamber and outflow channel). For example, a volume of the liquid suspension defined via a dispenser may be fed to the inflow channel inlet in the rest state or via an also rotating intermediate reservoir during rotation.

According to the invention, the rotation body may preferably be a disk in which the fluid structures are formed. The rotation body may further comprise a lid for closing the fluid structures to the top. Furthermore, in such a disk, a plurality of the inventive fluid structures may be formed, so that azimuthal parallelization takes place in that the inventive particle sedimentation apparatus is replicated azimuthally according to the rotation symmetry, and hence sequential and, in particular, also parallel processing of several liquid suspensions is possible.

BRIEF DESCRIPTION OF THE DRAWINGS

Preferred embodiments of the present invention will be detailed subsequently referring to the appended drawings, in which:

FIGS. 7a and 7b are schematic top views of a disk as a rotation body; and FIG. 8 is a schematic side view of a rotation body with rotation drive.

DETAILED DESCRIPTION

Figure 2:
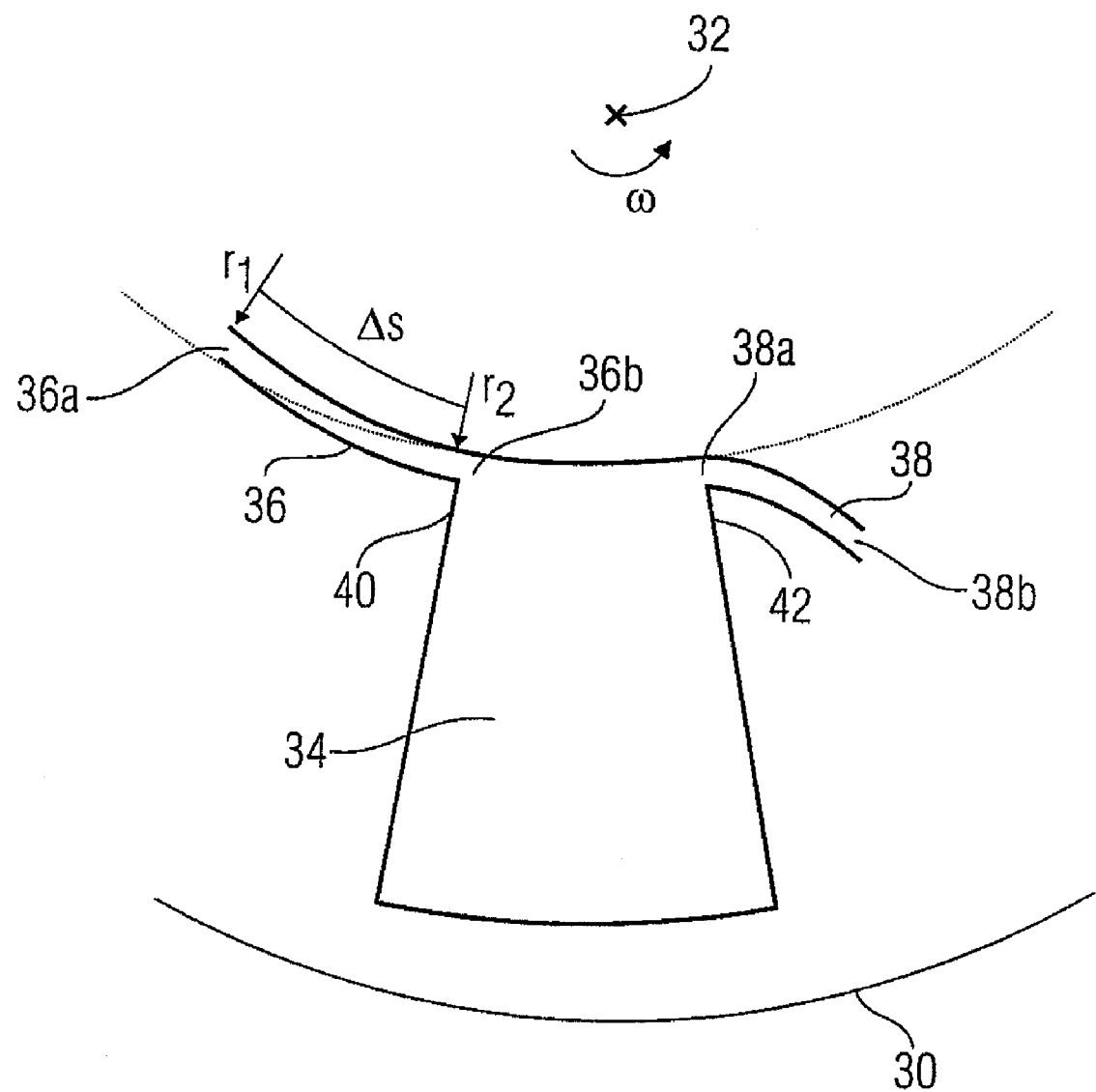
FIG. 2 is a schematic top view of an embodiment of an inventive particle sedimentation apparatus.

FIG. 2 shows a schematic top view onto an embodiment of a particle sedimentation apparatus according to the invention, on the basis of which the functional principle underlying the present invention will be explained in the following.

In FIG. 2, a rotation body 30 having a rotation axis 32 is shown schematically. Preferably, the rotation body is formed in rotation-symmetrical manner and is preferably formed by a disk. In the surface of the rotation body 30, fluid structures in the form of a separation chamber 34, an inflow channel 36 and an outflow channel 38 are formed. The inflow channel 36 has an inflow channel inlet 36a and an inflow channel outlet 36b fluidically connected to the separation chamber 34. The outflow channel 38 has an outflow channel inlet 38a connected to the separation chamber 34 fluidically and an outflow channel outlet 38b. The rotation body preferably comprises, apart from the disk in which the described fluidic structures are formed (and moreover further fluidic structures (not shown in FIG. 2) may be formed, which are connected to the inflow channel inlet 36a and the outflow channel outlet 38b), a lid for covering the fluidic structures. In other words, the channels are substantially closed, apart from the necessary inlets and outlets. As shown in FIG. 2, in the illustrated embodiment, the inflow channel 36 is fluidically connected, in a radially inner portion of the separation chamber 34, to the same. Furthermore, the outlet channel 38 is fluidically connected to the separation chamber 34 in a radially inner portion. Furthermore, the inflow channel is connected to the separation chamber on a first side 40, whereas the outflow channel 38 is connected to the separation chamber 34 on a second side. More specifically, in the illustrated embodiment, the first side 40 is the rear side in rotation direction, whereas the second side 42 is the front side in rotation direction.

The inflow channel 36 is rising in radial direction, i.e. the inflow channel inlet 36a is arranged radially further inward than the inflow channel outlet 36b. More specifically, the inner wall of the inflow channel in the region of the inlet thereof is arranged at a radius $r_1$, whereas the inner wall of the inflow channel 36 is arranged at a radius r2 at the outlet thereof.

Upon rotation of the rotation body 30 about the rotation axis 32 at a rotation velocity $\omega$, for example, liquid of a volume $V_0$, for example, is passed into the separation chamber 34, which may also be referred to as sedimentation chamber, by means of centrifugal force via the inflow channel 36 rising in radial r direction facing away from the rotation center at a flow rate $\Phi_{in}$. The inflow rate $\Phi_{in}$ changes with the square of the rotation frequency $\omega$ on the one hand and with the radial "slope", i.e. expressed in cylinder coordinates, the radial increase $\Delta r>0$ per azimuthal path length $\Delta s>0$ in flow direction. If the centrifugal field is illustrated as gravitational field of the Earth, a head of water with the density $\rho$ with the equivalent pressure $\rho g \Delta r$ develops, wherein the acceleration constant in the centrifugation is given by $\omega^2 r$. On the other hand, the inflow rate $\Phi_{in}$ changes with the reciprocal flow resistance $R_{in}$ of the inlet channel, which particularly depends on the cross-sectional area and the length of the inlet channel. Thus, the liquid level in the separation chamber 34 rises with a velocity of $u_{dec}(t)=\Delta r(t)/\Delta t=-\Phi_{in}/A<0$ (i.e. in direction of the rotation axis, i.e. toward the rotation center), corresponding to $\Phi_{in}$ and the cross-sectional area A of the separation chamber 34.

During the rotation, the interface between the particle-free supernatant and the sediment or the part of the volume comprising particles, i.e. in the non-equilibrium state suspension and sediment, drops with an opposite relative velocity $u_{drift}$. The velocity $u_{drift}$ here designates the velocity that would be observed at interrupted inflow $\Phi_{in}=0$. This relative velocity $u_{drift}$ is to be differentiated from the absolute rising velocity of this boundary layer $u_{abs}$. The difference between $u_{dec}$ and $u_{drift}$ goes into $u_{abs}$. Like $\Phi_{in}$, also $u_{drift}$ is proportional to the square of the rotation frequency $\omega$, so that at a given geometry the ratio of $u_{drift}$ to $\Phi_{in}$ is independent from the rotation speed $\omega$. Apart from $u_{drift}$, the shape of the interface on the inlet side is also dependent on the spatial and temporal course of the inflow during the centrifugal process.

Figure 1:
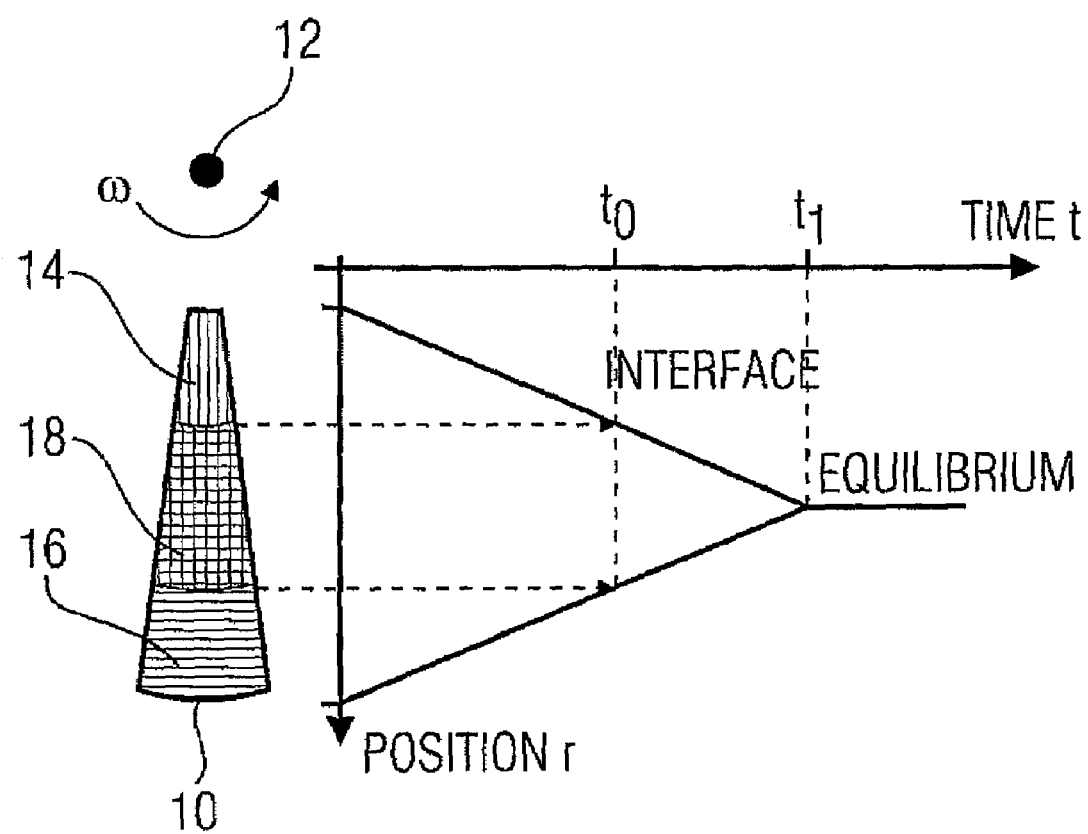
FIG. 1 is a schematic illustration for illustrating the effect underlying centrifugal sedimentation.
Figure 3A:
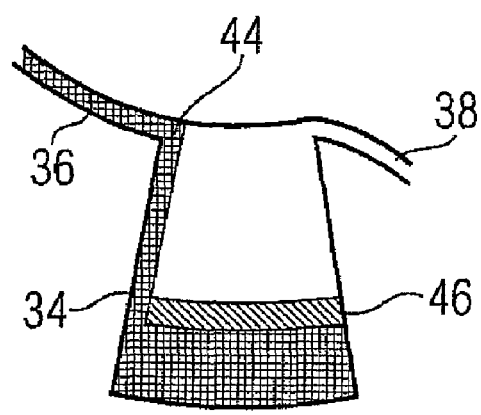
FIGS. 3a to 3c are schematic illustrations for illustrating the process flow in one embodiment of sedimentation according to the invention.

FIG. 3a schematically shows how a liquid suspension, for example blood, 44 is supplied in a first step via the inflow channel 36. In the separation chamber 34, sedimentation, as it was described above with reference to FIG. 1, takes place, wherein only the particle-free supernatant liquid 46 (for example the blood plasma) is illustrated separately from the other shown phase, which summarizes the particulate phases of the suspension and of the sediment, in FIGS. 3a to 3c for simplicity. By the centrifugal force, the inflow is forced along the wall of the separation chamber opposite the outflow, so that direct flow of the not yet (completely) sedimented inlet stream into the outlet is prevented.

Figure 3B:
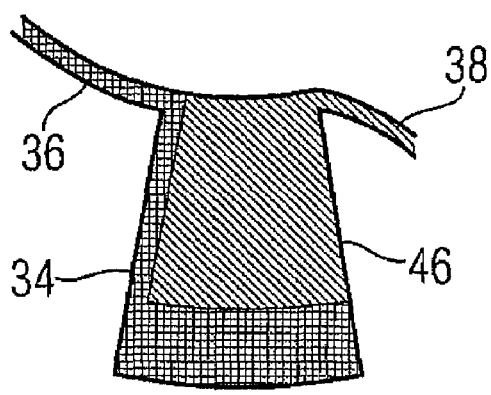

In FIG. 3b, the state in which suspension is still introduced into the separation chamber via the inflow channel 36 is shown, while particle-free supernatant liquid 46 is removed from the separation chamber via the outflow channel 38. Sedimentation, as described above with reference to FIG. 1, still takes place in the separation chamber.

Figure 3C:
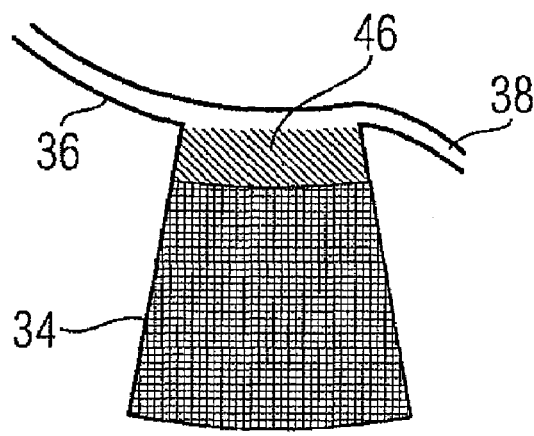

In FIG. 3c, finally the end state is illustrated, after a predetermined suspension volume has been sedimented by the sedimentation apparatus. The flow of the particle-free supernatant liquid drained off through the outflow channel 38 interrupts, when no suspension is supplied any more via the inflow channel 36 and the outflow channel inlet comes into communication with ambient gas, which for example penetrates via the inflow channel 36 (for example air at atmospheric pressure).

The arrangement of the outflow channel 38 with reference to the separation chamber 34 thus decisively determines the dead volume $V_{dead}$ of the channel structure, i.e. the media volume, which remains in the system after the centrifugation. The radially outward point of the orifice of the outflow channel 38 into the separation chamber 34, which may be referred to as $r_{min}$, determines the fill height of the separation chamber 34 after the centrifugation, and hence the dead volume $V_{dead}$ thereof.

With known volume of the suspension, which is supplied via the inflow channel 36, and known dead volume, hence a defined, known volume of the particle-free supernatant liquid can be issued via the outflow channel 38. The outflow channel 38 preferably rises at least starting from a certain point, but typically along its entire path, in radial manner so as to be able to empty itself completely via the centrifugation.

In summary, in a first step, the inlet channel is supplied with a liquid volume $V_0$ and made to rotate. The centrifugal force resulting therefrom acts like an artificial gravitational field, which on the one hand forces the flow "down" (to rising r) into the separation chamber due to the radial gradient $\Delta r/\Delta s>0$ of the inflow channel like on an inclined plane on the one hand. During the rotation, the particle suspension introduced is subject to continuous centrifugal separation, so that a phase interface rising radially with time forms in the separation chamber. Through the corresponding course of the outflow channel, the particle-free supernatant liquid is then drained off via the outflow channel 38.

Figure 4:
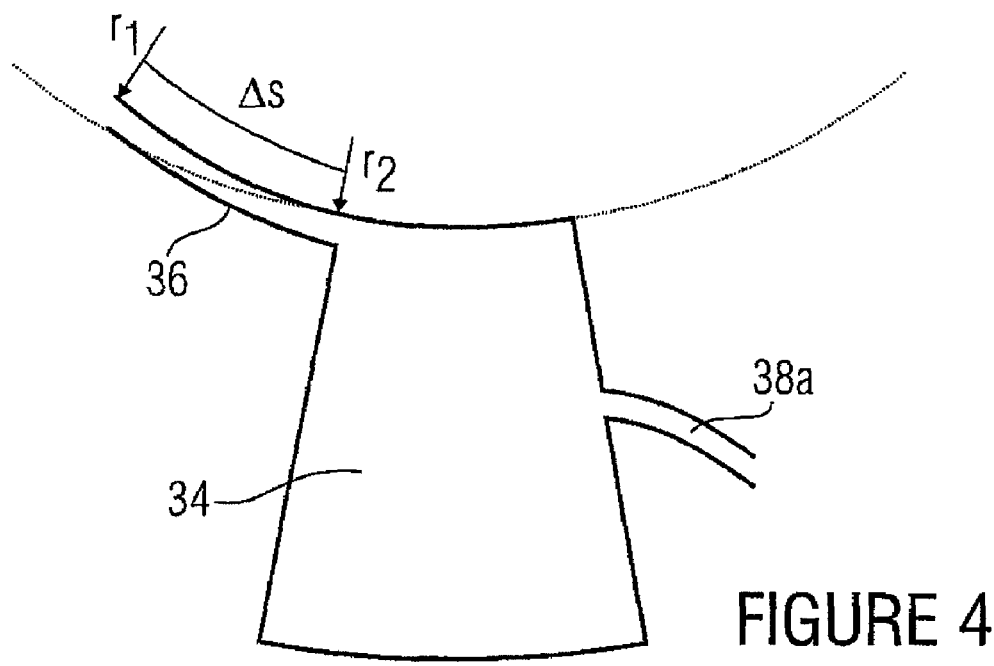
FIGS. 4 and 5 are schematic top views of alternative embodiments of the present invention.
Figure 5:
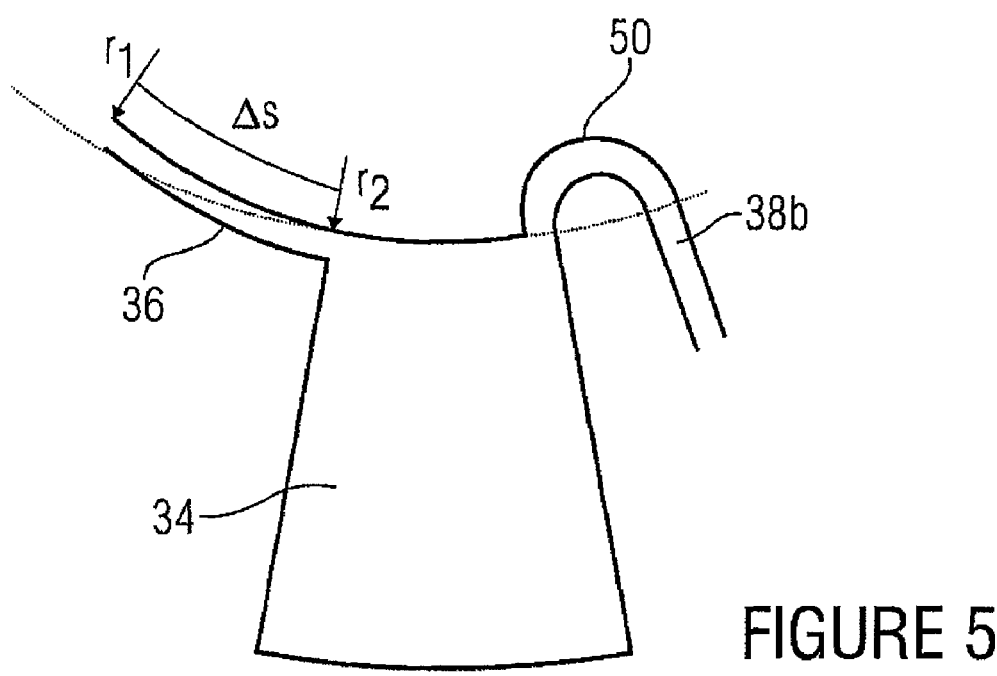

Alternative embodiments for a geometrical arrangement of the outflow channel are shown in FIGS. 4 and 5. According to FIG. 4, the outflow channel 38a is fluidically connected, in a radially inner region of the separation chamber 34, to the same, but not on the radial inside thereof.

In the embodiment shown in FIG. 5, the outflow channel 38b at first extends from a radially inner side of the separation chamber 34 radially inwardly, before the same extends radially outwardly after a radial minimum 50.

In the embodiments shown in FIGS. 2 and 4, in case the outflow channel inlet is accessible to ambient gas, for example air at atmospheric pressure, the radial minimum of the lower edge of the respective outflow channel 38 or 38a substantially gives the fill height after the centrifugation. In the embodiment shown in FIG. 5, the centrifugally driven flow at the outflow channel 38b sucks at the separation chamber 34 as long as the fill height in the outflow channel lies radially further outwardly than the fill height of the separation chamber, and no ambient gas can reach the flow in the outlet region. This sucking off may substantially influence the amount of liquid drained off through the outflow channel 38b. But since this sucking off may take place in reproducible manner, a defined volume of particle-free supernatant liquid may still be drained off at constant conditions.

Alternatively, in the region in which the outflow channel 38b leads into the separation chamber 34, access to the ambient gas could be provided, so that sucking from the separation chamber, as it is described above, does not take place after termination of suspension feed. To this end, for example, a hydrophobic hole could be provided in the lid of the rotation body in the region of the orifice of the outflow channel into the separation chamber. This enables the flow from the separation chamber to have a temporally continuous fluidic access to the ambient gas, in order to achieve a geometrically defined volume interruption.

The present invention is suited, in preferred embodiments thereof, particularly for implementation of sedimentation apparatus in which it can be ensured that the supernatant liquid is substantially particle free. For the functional principle of such embodiments, it is important that the dead volume $V_{dead}$ of the structure exceeds the volume of the centrifugated sediment $V_{sed}$. On the other hand, in such embodiments, the migration velocity of the overall liquid level $u_{dec}$ in the sedimentation chamber as opposed to the absolute radial migration velocity of this boundary layer $u_{abs}$ (on the outlet side) has to be so low that particles cannot reach any part of the outflow channel outside the dead volume at any time. In other words, at least for the case of gas addition to the outflow region, the height $r_{abs}$ of the interface (between supernatant liquid and particulate phase) must not lie radially further inward than $r_{min}$ at any time instant t. To this end, $u_{dec}$ may, for example, be choked via the hydrodynamic resistance $R_{in}$ of the inflow channel, i.e. its length and its cross-sectional area, as well as its slope $\Delta r/\Delta s$ and the cross section A of the separation chamber.

Figure 6:
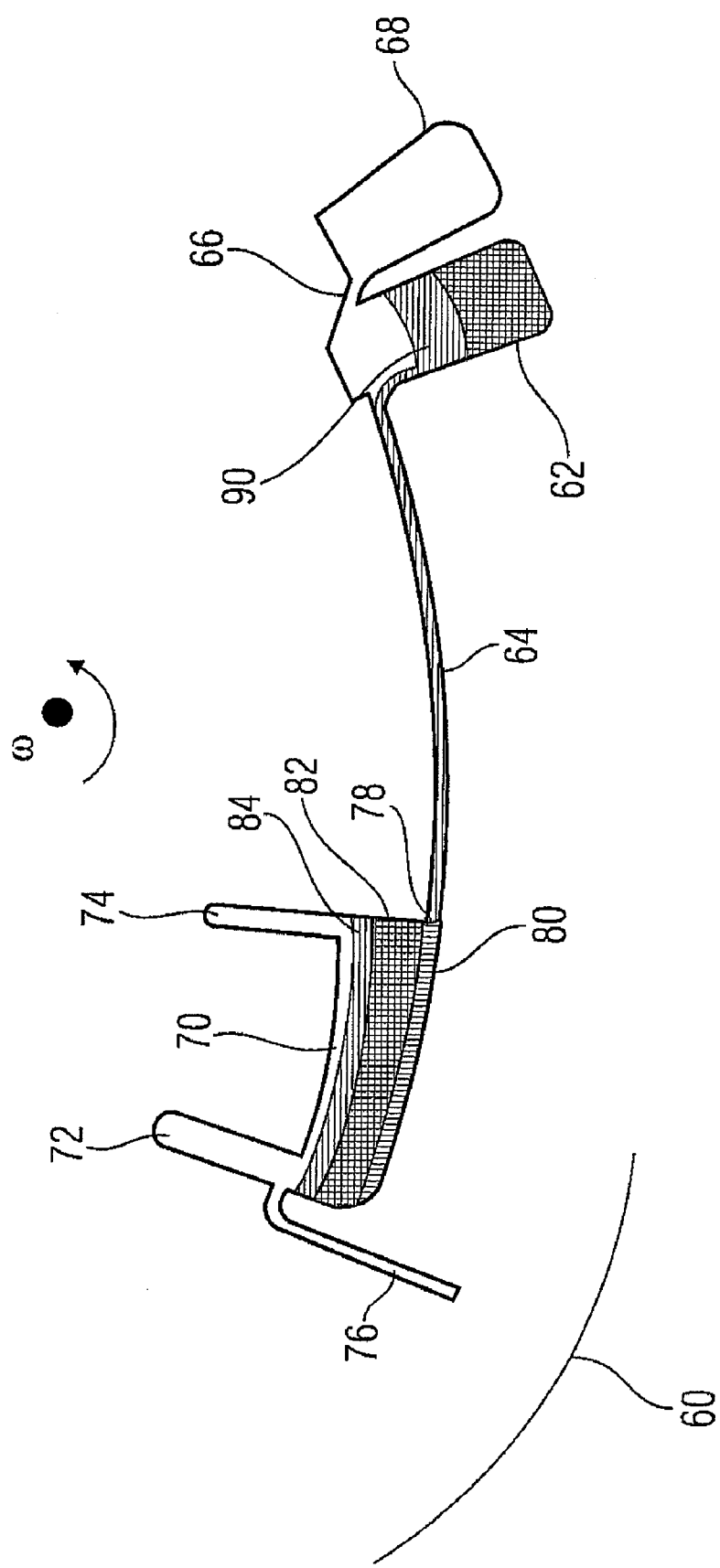
FIG. 6 is a schematic top view of a further alternative embodiment of the present invention.

One embodiment of an inventive sedimentation apparatus, the inflow channel and outflow channel of which are connected to further fluidic structures, is shown in FIG. 6. The fluidic structures shown in FIG. 6 are in turn arranged in a rotation body 60. In the rotation body 60, in turn a separation chamber 62, an inflow channel 64 and an outflow channel 66 are formed. The outlet of the outflow channel 66 is fluidically connected to a fluid chamber, for example a measurement chamber 68. The inlet of the inflow channel 64 is fluidically connected to a dosing chamber 70. The dosing chamber comprises an inlet 72, a vent 74 and an overflow 76. Furthermore, the outlet of the dosing chamber 70 to the inflow channel 64 is formed as a hydrophobized outlet 78. Via the inlet 72, a suspension, for example blood, can be introduced into the dosing chamber 70. Via the vent 74, which is facing radially inwardly, air bubbles can escape. The volume of the suspension introduced into the dosing chamber is defined by the hydrophobized outlet 78 and the radial position and the course of the overflow channel 76. The vent 74 allows for optimum, i.e. volume-defined, filling. Blood may for example be introduced into the dosing chamber, for example, at a rotation frequency ω of 10 Hz with a volume of 5 μl.

After the desired volume is introduced into the dosing chamber 70, the dosing chamber 70 gives off the volume $V_0$ defined via the chamber geometry and the height and the course of the overflow into the inflow channel 64 upon exceeding a geometrically defined rotational speed threshold. Here, for example, a rotation frequency of ω=40 Hz may be used. As indicated in FIG. 6, sedimentation with the resulting phases of sediment 80, suspension 82 and supernatant liquid 84 already arises in the chamber 70. At this point it is to be noted, however, that these phases are all fed into the separation chamber 62 as suspension via the inflow channel 64, wherein the sediment 80, in particular, is not compressed such that it could no longer be fed through the inflow channel 64.

The suspension fed via the inflow channel 64 reaches the separation chamber 62, where an increase of the liquid volume there takes place, and particle-free supernatant liquid 90 is produced within the scope of the sedimentation taking place. At a further rise of the liquid level, the supernatant liquid, for example the cleaned blood plasma, flows into the measurement chamber 68 via the outflow channel 66, whereas the sediment is held back at the bottom of the separation chamber 62.

In FIG. 7a, a rotation body of an embodiment of an inventive particle sedimentation apparatus is schematically illustrated as a disk 92. The disk may be constructed according to the type of a conventional CD, with a center opening 94, by means of which it may for example be attached to a conventional centrifuge. The fluid structures of an inventive particle sedimentation apparatus are shown in FIG. 7a purely schematically, wherein the fluid structures 96 may for example include those shown in FIG. 6.

In FIG. 7b, an embodiment is shown, in which a plurality of fluidic structures 96 are formed in a rotation disk 92a, in order to achieve parallelization.

Finally, FIG. 8 shows an embodiment of a particle sedimentation apparatus comprising a rotation body including a disk 92 and a lid 98. The rotation body is attached to a rotating part 102 of a driving device, which is pivoted to a stationary part 104 of the driving device, via mounting means 100. The driving device may for example be a conventional centrifuge with adjustable rotation speed.

Instead of the dosing chamber described above with reference to FIG. 6, arbitrary dosing apparatus or dispensers suited to introduce a defined suspension volume into the inflow channel inlet may be used. The rotation body of the inventive particle sedimentation apparatus may consist of any suitable materials, for example plastics, silicon, metal or the like, and may be produced by any suitable production method, for example micro-structuring or injection molding techniques.

The present invention provides a novel method based on centrifugal force for continuous (temporally limited) extraction of particle-free supernatant liquid from a sediment, which may be advantageously implemented in a three-stage microfluidic structure, wherein the continuous extraction ends with the dosed particle-free supernatant liquid, which is easily available for subsequent on-disk processing. For example, it has turned out that the present invention is advantageously employable to separate blood plasma from cell sediment, wherein for example 2 µl of plasma can be separated from 5 µl of blood at low rotation frequencies of up to 40 Hz in only 20 seconds. It has turned out that the residual cell concentration in the cleaned plasma can be kept below one percent largely independently of the rotation frequency.

As set forth above, draining off substantially particle-free supernatant liquid can be achieved when the dead volume of the separation chamber is slightly greater than the volume of the cells, i.e. of the sediment. In this manner, only cleaned plasma flows off via the outflow channel, for example into a subsequent reservoir, in which it is available for further processing. Moreover, substantially particle-free supernatant liquid may then be obtained, when the flow resistance of the inflow channel and the geometry of the separation chamber are adjusted so as to make the rise velocity of the fill height, $u_{dec}$, substantially smaller than the opposite velocity $u_{drift}$, and so that in case of possible gas addition to the inlet of the outflow channel it is ensured, by the migration velocity $U_{abs}$, that the radially outer boundary of the supernatant liquid does not come to lie radially further inward than the radially outer boundary ($r_{min}$) of the outflow channel inlet. Since both $u_{dec}$ and $u_{drift}$ change with the square of the rotation frequency $\omega$, the efficiency of the separation does not depend on the rotation frequency. Moreover, the separation time $t_{sep}$ in this centrifugation scheme is controlled by the flow resistance of the inflow channel.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A method for performing sedimentation of a particle suspension, using micro-fluidic structures comprising an inflow channel comprising an azimuthal path length and determining the flow rate, wherein an inflow channel inlet is arranged radially further inwardly than an inflow channel outlet, as well as a separation chamber with a particle accumulation region, and an outflow channel, which are formed in a rotation body, wherein a portion of the inflow channel with an azimuthal path length leads into the separation chamber, comprising:

imparting the rotation body with rotation at the given rotation frequency, in order to feed a defined particle suspension volume by centrifugal force through the inflow channel into the separation chamber at a position radially inward with respect to the particle accumulation region;

sediment the particle suspension in the separation chamber, so that particles accumulate in a radially outward particle accumulation region of the separation chamber due to their higher mass density as compared with a liquid in the particle suspension; and at least partially draining off supernatant liquid developing by the sedimentation by centrifugal force through an outflow channel fluidically connected to the separation chamber, wherein the inflow channel comprises such a radial slope, such a length and such a cross section that, at a given rotation frequency and the defined particle suspension volume, the flow rate of the particle suspension into the separation chamber is so low that an inflow of a particulate phase in the separation chamber is forced along a wall spaced from an outflow channel inlet, so that an interface forming between supernatant liquid and a particulate phase in the separation chamber remains radially outside an outflow channel inlet, at which the outflow channel is fluidically connected to the separation chamber.

2. The method according to claim 1, further comprising dosing the known given volume by a dosing chamber.

3. The method according to claim 1 or 2, comprising a step of leaving a dead volume in the separation chamber, so that a defined predetermined volume of the supernatant liquid is drained off in the step of draining off.

* * * * *